(12) United States Patent
Harris et al.

(10) Patent No.: US 6,423,721 B1
(45) Date of Patent: Jul. 23, 2002

(54) METHODS AND COMPOSITIONS FOR TREATING SINUSITIS, OTITIS MEDIA AND OTHER RELATED DISORDERS USING ANTIHISTAMINES

(75) Inventors: Alan G. Harris, New York, NY (US); Domenic G. Iezzoni, Ridgewood, NJ (US); Melvyn R. Danzig, Morganville, NJ (US); Richard R. Lorber, Scotch Plains, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/391,795

(22) Filed: Sep. 9, 1999

Related U.S. Application Data

(60) Provisional application No. 60/099,682, filed on Sep. 10, 1998.

(51) Int. Cl.$^7$ ................................................ A61K 31/44
(52) U.S. Cl. ..................................................... 514/290
(58) Field of Search ......................................... 514/290

(56) References Cited

U.S. PATENT DOCUMENTS 4,282,233 A    8/1981   Villani
4,659,716 A    4/1987   Villani et al.
5,869,479 A  *  2/1999   Kreutner et al. ............ 514/212

OTHER PUBLICATIONS

*Conn's Current Therapy*, 235 (1997).
*Diseases of the Sinuses–A Comprehensive Textbook of Diagnosis and Treatment*, ed. M. E. Gershwin et al, Human Press, Totowa, New Jersey (1996), pp. 151–157.
*Allergy–Principles and Practice*, vol. II, ed. E. Middleton, Jr. et al, Mosby–Year Book, Inc., New York (1998), pp. 1027–1033.
Z. Pelikan, "The Role of Allergy in Sinus Disease", *Clinical Reviews in Allergy and Immunology* (1998) 16, 55–156.
J. Braun et al, *Allergy* (1997) 52 (6), 650–655.
Quercia et al, *Hosp. Formul.,* (1993) 28, 137–153.

* cited by examiner

*Primary Examiner*—Zohreh Fay
(74) *Attorney, Agent, or Firm*—Palaiyur S. Kalyanaraman

(57) ABSTRACT

The present invention discloses antibiotic-excluded compositions and methods to treat non-infective sinusitis and/or otitis media. The compositions comprise a therapeutically effective amount of an anticholinergic antihistamine or a pharmaceutically acceptable salt or solvate thereof; and (ii) a pharmaceutically acceptable carrier, and the methods comprise administering the same.

8 Claims, No Drawings

METHODS AND COMPOSITIONS FOR TREATING SINUSITIS, OTITIS MEDIA AND OTHER RELATED DISORDERS USING ANTIHISTAMINES

This app is a prov of 60/099,682 Sep. 10, 1998.

FIELD OF THE INVENTION

The present invention generally relates to methods of treatment of sinusitis and otitis media (including otitis media with effusion and persistent middle ear effusion) involving the administration of a therapeutically effective amount of an antihistamine. It specifically relates to such treatment involving the administration of a therapeutically effective amount of loratadine or its metabolic derivative known as descarboethoxyloratadine (also referred to as desloratadine or "DCL"). The invention disclosed herein is related to that disclosed in pending U.S. Patent application, Serial No. 60/068,638, filed Dec. 23, 1997.

BACKGROUND OF THE INVENTION

Sinusitis is the most frequently reported chronic disease in the United States, affecting more than 14% of the population. Sinusitis is an inflammation of the mucosa of the paranasal sinuses. Generally, there is an allergic cause to sinusitis. Otitis media, like sinusitis, is also generally considered to have an allergic cause. These are also characterized by retention of thickened respiratory secretions; however, the inflammation is manifest in the ear rather than in the sinuses. A discussion of sinusitis and otitis media can be found in *Conn's Current Therapy*, 235 (1997); *Diseases of the Sinuses—A Comprehensive Textbook of Diagnosis and Treatment,* ed. M. E. Gershwin et al, Human Press, Totowa, N.J., pages 151–157 (1996); and *Allergy-Principles and Practice,* Volume II, ed. E. Middleton, Jr. et al, Mosby-Year Book, Inc., New York, pages 1027–1033 (1998). Also, a review of sinusitis and related facts is given by Z. Pelikan, "The Role of Allergy in Sinus Disease", *Clinical Reviews in Allergy and Immunology* 16, 55–156 (1998).

Sinusitis and otitis media are often typically treated as an infectious disease. The treatment typically includes administration of an antibiotic along with a corticosteroid and an antihistamine, or a nasal decongestant, such as described in, for example, J. Braun et al, *Allergy,* 52 (6), 650–655 (1997). There are, however, occasions, when the sinusitis or otitis media is not necessarily accompanied by an infection. This is particularly true when the disease is associated with allergic rhinitis. At those times, administration of an antibiotic may not be needed. Physicians, however, do not generally administer antihistamines for these indications without accompanying antibiotic. This has been so since earlier known antihistamines, among other things, were anticholinergic, drying nasal secretions. Although antihistamines with far less anticholinergic activity are now available, no attempt to treat sinusitis or otitis media with administration of substantially non-sedating antihistamine with non-anticholinergic or reduced anticholinergic activity and without accompanying antibiotics has been reported.

It would be desirable to find methods of treatment for non-infective sinusitis or otitis media using an effective amount of substantially an antihistamine as an active ingredient in the absence of antibiotics.

It would be further desirable to find methods of treatment for non-infective sinusitis or otitis media using an effective amount of substantially an antihistamine with reduced anticholinergic activity as an active ingredient in the absence of antibiotics.

Other desires, objectives and advantages of the present invention will be apparent o those skilled in the art from the accompanying description and claims.

SUMMARY OF THE INVENTION

The above-noted desires and objectives are addressed by the present invention which, in one embodiment, provides methods and pharmaceutical compositions for the treatment of non-infectious sinusitis or otitis media or both. The composition comprises in combination: (i) a therapeutically effective amount of one or more antihistamines with substantially reduced anticholinergic activity or a pharmaceutically acceptable salt or solvate of such antihistamine(s) and (ii) a pharmaceutically acceptable carrier. While additional ingredient or ingredients may optionally be present, the antihistamine(s) is (are) the major active ingredient(s) in the composition. Antibiotics, however, are absent in the composition. The antihistamines useful in the practice of the present invention correspond to the general Formula I:

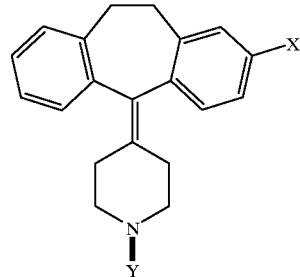

Formula I wherein X represents a halogen atom or a hydrogen atom; and Y represents hydrogen, —COOR$_1$ or —SO$_2$R$_2$, wherein R$_1$ represents a substituted or unsubstituted alkyl group, a substituted or unsubstituted cycloalkyl group, a substituted or unsubstituted alkenyl group, a substituted or unsubstituted aryl group, or a substituted or unsubstituted heterocyclic ring; and R$_2$ represents a substituted or unsubstituted cycloalkyl group, or substituted or unsubstituted aryl group. The compounds of Formula I embrace optical isomers and mixtures thereof, racemic mixtures, enol forms and other such modifications. Preferred compounds belonging to Formula I are those in which X is a halogen atom or a hydrogen atom, and Y is hydrogen or —COOR$_1$, where R$_1$ is defined above. More particularly preferred compounds of this class are when X is Cl and R$_1$ is carboethoxy (the compound being commonly known as loratadine or SCH 29851) and when X is Cl and R$_1$ is hydrogen (the compound being commonly known as descarboethoxyloratadine or desloratadine or DCL or SCH 34117).

The antihistamine or its pharmaceutically acceptable salt or solvate is generally present in the composition in about 2.5–20 milligrams, preferably in about 5–10 milligrams and typically in about 7.5 milligrams per dosage. Additionally, a pharmaceutically acceptable carrier is present. As stated earlier, one or more other non-antibiotic ingredients may also be optionally present in the composition. Such optional compounds may include, a decongestant (such as, for example, pseudoephedrine), a cough suppressant (such as, for example, dextromethorphan), an expectorant (such as, for example, guiaifenesin), a leukotriene antagonist (such as, for example, montelukast or a pharmaceutically acceptable salt or solvate thereof, and the like), an inhaled nasal steroid (such as, for example, mometasone furoate, NASONEX*

(available from Schering-Plough Corporation, Madison, N.J.) and the like), a non-steroidal anti-inflammatory (such as, for example, ibuprofen, naproxen and the like), a non-narcotic analgesic (such as, for example, acetaminophen and the like) and suitable combinations thereof.

The present invention additionally discloses a method for the treatment of non-infectious sinusitis and/or otitis media in a mammalian organism in need of such treatment, such treatment comprising administering a pharmaceutical composition described above.

DESCRIPTION OF THE INVENTION

In one embodiment, this invention provides pharmaceutical compositions for the treatment of non-infectious sinusitis, otitis media or both. The term "otitis media" also includes otitis media with effusion and persistent middle ear effusion in this invention. The composition comprises a therapeutically effective amount of one or more antihistamines with substantially reduced anticholinergic activity or a pharmaceutically acceptable salt or solvate of such antihistamine, in combination with a pharmaceutically acceptable carrier. While additional ingredients may optionally be present, the antihistamine is the major active ingredient in the composition. Antibiotics, however, are absent in the composition. The amount of the antihistamine which can be employed in a unit dosage form of the present compositions ranges generally from about 2.5 to about 20 mg, preferably from about 5 to about 10 milligrams and typically in about 7.5 milligrams.

The antihistamines useful in the practice of the present invention correspond the general Formula I shown above. The various elements in Formula I are also described above. The compounds of Formula I can be prepared in accordance with processes known in the art, for example, that disclosed in U.S. Pat. No. 3,326,924. Preferred compounds are those in which X is a halogen atom or a hydrogen atom, and Y is hydrogen or —$COOR_1$, where $R_1$ is defined above. More particularly preferred compounds of this class are when X is Cl and $R_1$ is carboethoxy (the compound being known as loratadine) and when X is Cl and $R_1$ is hydrogen (the compound being known as descarboethoxyloratadine or DCL).

Loratadine is an antagonist of the H-1 histamine receptor protein. The histamine receptors H-1 and H-2 are two well-identified forms. The H-1 receptors are those that mediate the response antagonized by conventional antihistamines. H-1 receptors are present, for example, in the nose, sinus, ocular conjunctiva and tissues, ileum, the skin, and the bronchial smooth muscle of man and other mammals.

Descarboethoxyloratadine (DCL) is a non-sedating antihistamine, whose technical name is 8-chloro-6,11-dihydro-11-(4-piperidylidene)-5H-benzo[5,6]cyclohepta[1, 2]pyridine. This compound is described in Quercia et al., Hosp. Formul., 28, 137–53 (1993), in U.S. Pat. No. 4,659, 716, and in WO 96/20708. DCL is also an antagonist of the H-1 histamine receptor protein. DCL is a metabolic derivative of loratadine.

As stated earlier, a pharmaceutically acceptable carrier (which includes diluents, excipients or carrier materials) is also present in the composition. The carrier is suitably selected with respect to the intended form of administration, i.e. oral tablets, capsules (either solid-filled, semi-solid filled or liquid filled), powders for constitution, oral gels, elixirs, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, mannitol, ethyl alcohol (liquid forms) and the like. Moreover, when desired or needed, suitable binders, lubricants, disintegrating agents, disinfectants and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Disinfectants include benzalkonium chloride and the like. Sweetening and flavoring agents and preservatives may also be included where appropriate.

Other non-antibiotic ingredients may also be optionally present in the composition. Such optional compounds may include a decongestant (such as, for example, pseudoephedrine), a cough suppressant (such as, for example, dextromethorphan), an expectorant (such as, for example, guiaifenesin), a leukotriene antagonist (such as, for example, montelukast or a pharmaceutically acceptable salt thereof), an inhaled nasal steroid (such as, for example, mometasone furoate, NASONEX* and the like), a non-steroidal anti-inflammatory (such as, for example, ibuprofen, naproxen and the like), a non-narcotic analgesic (such as, for example, acetaminophen and the like) and suitable combinations thereof, such as, for example, a nasal spray with a combination of ingredients including loratadine, DCL, mometasone furoate and other suitable ingredients.

In another embodiment, the present invention discloses a method of preparing a composition for the treatment of sinusitis and/or otitis media, with the composition comprising a therapeutically effective amount of one or more antihistamines represented by Formula I, or a pharmaceutically acceptable salt or solvate of such antihistamine, in combination with a pharmaceutically acceptable carrier.

In yet another embodiment, the present invention discloses a method of administering an effective treatment for sinusitis and/or otitis media. The pharmaceutical compositions of the present invention can be administered depending upon the patient's age, sex, weight and severity of the condition being treated. Generally, the human oral dosage form containing the antihistamine and the carrier can be administered 1 or 2 times per day.

In a further embodiment, this invention discloses a method for the treatment of non-infectious sinusitis and/or otitis media in a mammalian organism in need of such treatment, such treatment comprising administering a pharmaceutical composition described above.

Additionally, the compositions of the present invention may be formulated in sustained release form to provide the rate controlled release of any one or more of the components or active ingredients to optimize the therapeutic effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Dosage form—refers to composition containing the antihistamine and the carrier formulated into a delivery system, i.e., tablet, capsule, oral gel, powder for constitution or suspension in association with inactive ingredients.

Capsule—refers to a special container or enclosure made of methyl cellulose, polyvinyl alcohols, or denatured gelatins or starch for holding or containing compositions comprising the antihistamine and the carrier. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the ingredients (the antihistamine and the carrier) with suitable diluents. The tablet can be prepared by compression of mixtures or granulations obtained by wet granulation, dry granulation or by compaction.

Oral gels—refers to the antihistamine and the carrier dispersed or solubilized in a hydrophilic semi-solid matrix.

Powders for constitution refers to powder blends containing the antihistamine and the carrier and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidinone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control, as well as to topical bioavailability.

Conventional methods for preparing tablets are known. Such methods include dry methods such as direct compression and compression of granulation produced by compaction, or wet methods or other special procedures.

The antihistamine/carrier combination and the optional ingredient or ingredients may be administered in combination or separately in the method of treating the non-infective sinusitis or otitis media. For example, they may be administered concurrently or sequentially, i.e. they may be administered in combination either concurrently or by the sequential administration of the ingredients in a suitable order.

The phrase "therapeutically effective amount" means that amount of the antihistamine which provides a therapeutical benefit in the treatment or management of the non-infective sinusitis or otitis media.

The magnitude of a prophylactic or therapeutic dose of the antihistamine in the acute or chronic management of the targeted disease or condition will vary with the severity of the condition to be treated and the route of administration. The dose, and perhaps the dose frequency, will also vary according the age, body weight, and response of the individual patient. Suitable total daily dose ranges can be readily determined by those skilled in the art. The dose may be administered in single or divided doses orally, topically, transdermally, or locally by inhalation. A preferred oral daily dose range of decongestant, such as pseudophedrine, should be from about 50 mg to about 300 mg, more preferably, about 120 mg to about 240 mg. In addition, suitable oral daily dosage ranges of leukotriene inhibitor can be readily determined by those skilled in the art.

It is further recommended that children, patients aged over 65 years, and those with impaired renal or haptic function initially receive low doses, and that they then be titrated based on individual response(s) or blood level(s). Further, it is noted that the clinician or treating physician will know how and when to adjust, interrupt, or terminate therapy in conjunction with individual patient response.

Any suitable route of administration may be employed for providing the patient with an effective dosage of the antihistamine according to the methods of the present invention. For example, oral, intraoral, rectal, parenteral, epicutaneous, transdermal, subcutaneous, intramuscular, intranasal, sublingual, intradural, intraocular, intrarespiratory, oral or nasal inhalation and like forms of administration may be employed. For the methods to treat dermatitis topical administration is preferred.

The term "pharmaceutically acceptable salt" refers to a salt prepared from pharmaceutically acceptable non-toxic acids or bases including inorganic acids or bases or organic acids or bases. Examples of such inorganic acids are hydrochloric, hydrobromic, hydroiodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, algenic, and galacturonic. Examples of such inorganic bases include metallic salts made from aluminum, calcium, lithium, magnesium, potassium, sodium, and zinc. Appropriate organic bases may be selected, for example, from N,N-dibenzylethylenediamine, chloroprocaine, choline, diethanolamine, ethylenediamine, meglumaine (N-methylgulcaine), lysine and procaine.

As stated before, dosage forms include tablets, troches, dispersions, suspensions, solutions, capsules, patches, syrups, elixirs, gels, powders, magmas, lozenges, ointments, creams, pastes, plasters, lotions, discs, suppositories, nasal or oral sprays, aerosols and the like. Because of their ease of administration, tablets and capsules represent the most advantageous oral dosage unit form, in which case solid pharmaceutical carriers are employed. If desirable, tablets may be coated by standard aqueous or nonaqueous techniques.

In addition to the common dosage forms set out above, the composition for use in the methods of the present invention may also be administered by controlled release means and/or delivery devices. Such skills are well known to those skilled in the art.

Pharmaceutical compositions for use in the methods of the present invention may be prepared by any of the methods of pharmacy, but all methods include the step of bringing into association the active ingredient and any optional ingredient or ingredients with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent.

As stated earlier, the antihistamines particularly preferred in the practice of the invention are loratadine and its metabolite, DCL. Loratadine may be synthesized by methods disclosed in U.S. Pat. No. 4,282,233. The metabolite DCL may be prepared similarly, by reaction steps conventional in the art, as described in U.S. Pat. No. 4,659,716 which is incorporated here by reference in its entirety. One common method of preparing DCL is to reflux loratadine in the presence of sodium hydroxide and ethanol. Various modifications of the invention in addition to those shown and described herein will be apparent to those skilled in the art from the forgoing description. Such modifications are also intended to fall within the scope of the appended claims.

What is claimed is:

1. A method for the treatment of non-infective sinusitis or otitis media or both in a mammalian organism in need of such treatment comprising administering a pharmaceutical composition comprising: (i) a therapeutically effective amount of descarboethoxyloratadine, optical isomers of said descarboethoxyloratadine or a pharmaceutically acceptable salt or solvate thereof; and (ii) a pharmaceutically acceptable carrier, said composition excluding an antibiotic.

2. The method of claim 1 for treating sinusitis.

3. The method of claim 1 for treating otitis media.

4. The method of claim 1, wherein descarboethoxyloratadine said is present in amounts in the range 2.5–20 milligrams per dosage.

5. The method of claim 2, wherein said descarboethoxyloratadine is present in amounts in the range 2.5–10 milligrams per dosage.

6. The method of claim 1, wherein said descarboethoxyloratadine is present in about 7.5 milligrams amounts per dosage.

7. The method of claim 1, wherein said pharmaceutically acceptable carrier is selected from the group consisting of lactose, sucrose, sugar, cellulose, magnesium stearate, dicalcium phosphate, calcium sulfate, mannitol, ethyl alcohol and mixtures thereof.

8. The method of claim 1, wherein said pharmaceutical composition further comprises one or more ingredients selected from the group consisting of a decongestant, a cough suppressant, an expectorant, a nasal steroid and a non-narcotic analgesic.

* * * * *